(12) United States Patent
Verlaak et al.

(10) Patent No.: US 11,439,759 B2
(45) Date of Patent: Sep. 13, 2022

(54) MEDICAMENT DELIVERY DEVICE

(71) Applicant: SANOFI-AVENTIS DEUTSCHLAND GMBH, Frankfurt am Main (DE)

(72) Inventors: Stefan Verlaak, Paderno d'Adda (IT); Ilario Melzi, Milan (IT)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 372 days.

(21) Appl. No.: 16/471,858

(22) PCT Filed: Dec. 21, 2017

(86) PCT No.: PCT/EP2017/084147
§ 371 (c)(1),
(2) Date: Jun. 20, 2019

(87) PCT Pub. No.: WO2018/115313
PCT Pub. Date: Jun. 28, 2018

(65) Prior Publication Data
US 2020/0086055 A1    Mar. 19, 2020

(30) Foreign Application Priority Data
Dec. 23, 2016    (EP) .................................. 16206618

(51) Int. Cl.
*A61M 5/315* (2006.01)
*A61M 5/145* (2006.01)
*A61M 5/31* (2006.01)

(52) U.S. Cl.
CPC ...... *A61M 5/31511* (2013.01); *A61M 5/1452* (2013.01); *A61M 2005/3126* (2013.01); *A61M 2005/3152* (2013.01)

(58) Field of Classification Search
CPC ............ A61M 5/31511; A61M 5/1452; A61M 2005/3126; A61M 2005/3152; A61M 5/31525; A61M 15/0073
See application file for complete search history.

(56) References Cited

U.S. PATENT DOCUMENTS

| 4,931,041 A | 6/1990 | Faeser | |
| 7,766,188 B2 * | 8/2010 | Pocock | G06M 1/248 222/36 |

(Continued)

FOREIGN PATENT DOCUMENTS

| CN | 204395143 | 6/2015 |
| CN | 105377331 | 3/2016 |

(Continued)

OTHER PUBLICATIONS

International Preliminary Report on Patentability in International Appln. No. PCT/EP2017/084147, dated Jun. 25, 2019, 8 pages.

(Continued)

*Primary Examiner* — Bradley J Osinski
(74) *Attorney, Agent, or Firm* — Fish & Richardson P.C.

(57) ABSTRACT

A medicament delivery device comprising: a housing arranged to contain a medicament container with a piston for sealing the medicament container and displacing the medicament; a medicament delivery mechanism arranged to push the piston to displace the medicament when activated; and a driving mechanism connected to the medicament delivery mechanism such that when the medicament delivery mechanism is activated, the driving mechanism converts linear motion of the medicament delivery mechanism into torque so as to rotate a rotation member.

8 Claims, 6 Drawing Sheets

(56) References Cited

U.S. PATENT DOCUMENTS

| | | | |
|---|---|---|---|
| 2005/0197625 A1* | 9/2005 | Haueter | A61M 5/1454 604/131 |
| 2007/0135756 A1 | 6/2007 | Kohlbrenner et al. | |
| 2016/0058949 A1 | 3/2016 | Bayer et al. | |

FOREIGN PATENT DOCUMENTS

| | | |
|---|---|---|
| JP | 2005-537112 | 12/2005 |
| JP | 2007-160095 | 6/2007 |
| JP | 2010-522577 | 7/2010 |
| JP | 2012-521818 | 9/2012 |
| JP | 2012-521819 | 9/2012 |
| WO | WO 2004/024218 | 3/2004 |
| WO | WO 2008/058666 | 5/2008 |
| WO | WO 2010/112376 | 10/2010 |
| WO | WO 2010/112377 | 10/2010 |
| WO | WO 2015/007810 | 1/2015 |
| WO | WO 2015/166286 | 11/2015 |

OTHER PUBLICATIONS

International Search Report and Written Opinion in International Appln. No. PCT/EP2017/084147, dated Mar. 27, 2018, 10 pages.

* cited by examiner

MEDICAMENT DELIVERY DEVICE

CROSS REFERENCE TO RELATED APPLICATIONS

The present application is the national stage entry of International Patent Application No. PCT/EP2017/084147, filed on Dec. 21, 2017, and claims priority to Application No. EP 16206618.7, filed on Dec. 23, 2016, the disclosures of which are incorporated herein by reference.

TECHNICAL FIELD

The disclosure relates to a device for delivery of medicament to a patient.

BACKGROUND

A variety of diseases exist that require regular treatment by injection of a medicament and such injections can be performed by using injection devices. Various injection devices for delivering injections of medicament are known in the art. Another type of injection pump that is gaining traction is the bolus injector device. Some bolus injector devices are intended to be used with relatively large volumes of medicament, typically at least 1 ml and maybe a few ml. Injection of such large volumes of medicament can take some minutes or even hours. Such high capacity bolus injector devices can be called large volume devices (LVDs). Generally such devices are operated by the patients themselves, although they may also be operated by medical personnel.

To use an injector device, such as an LVD, it is first supported on a suitable injection site on a patient's skin. Once installed, injection is initiated by the patient or another person (user). Typically, the initiation is effected by the user operating an electrical switch, which causes a controller to operate the device. Operation includes firstly injecting a needle into the user and then causing the injection of medicament into the user's tissue. Biological medicaments are being increasingly developed which comprise higher viscosity injectable liquids and which are to be administered in larger volumes than long-known liquid medicaments. LVDs for administering such biological medicaments may comprise a pre-filled disposable drug delivery device or, alternatively, a disposable drug delivery device into which a patient or medical personnel must insert a drug cartridge prior to use.

In some patient-operated LVDs, the drug delivery process from start to finish may be a lengthy process and sometimes it is difficult for the patient to determine whether the injection process is complete. Some medicament delivery devices are provided with on-board equipment including light sources and indicator systems for indicating the amount of medicament currently contained within the device or whether the medicament container is empty. In some of these devices with on-board equipment, batteries are provided so as to power the on-board equipment. However, these devices are often stored for a relatively long time before being used for delivering medicament. A problem is that, during this time of storage, battery corrosion and leakage may occur.

SUMMARY

According to an aspect of the present invention, there is provided a medicament delivery device comprising: a housing arranged to contain a medicament container with a piston for sealing the medicament container and displacing the medicament; a medicament delivery mechanism arranged to push the piston to displace the medicament when activated; and a driving mechanism connected to the medicament delivery mechanism such that when the medicament delivery mechanism is activated, the driving mechanism converts linear motion of the medicament delivery mechanism into torque so as to rotate a rotation member.

The rotation member may be connected to an indicator system.

The indicator system may comprise an indicator member and a scale, wherein the indicator member is arranged at the rotation member such that rotation of the rotation member causes the indicator member to move along the scale to indicate an amount of medicament contained in the medicament container.

A first end of the scale may represent a full medicament container and a second end of the scale may represent an empty medicament container.

The rotation member may be a gear wheel connected to an energy generating apparatus.

The energy generating apparatus may comprise a dynamo.

The medicament delivery device may further comprise a light source, wherein the light source is powered by the energy generating apparatus.

The driving mechanism may comprise a plate member arranged between the driving mechanism and the piston.

The driving mechanism may further comprise a first pulley, a cable passed over a periphery of the first pulley, and wherein the cable passes over the rotation member.

The driving mechanism may further comprise a first pulley, a cable passed over a periphery of the first pulley, a gear rack connected to the cable, and a first pinion gear rotatably engaged with the gear rack, wherein the plate member is fixedly attached to the cable and the first pinion gear is rotatably engaged with the first gear wheel.

The driving mechanism may further comprise a second pulley, and the cable may be passed over a periphery of the second pulley and the second pulley is configured to move the rack gear.

The medicament delivery device may be a bolus injector.

The medicament container may contain a liquid medicament.

According to an aspect of the present invention, there is provided a method of providing torque to a rotation member in a medicament delivery device, wherein an activation of a medicament delivery mechanism causes a driving mechanism connected to the medicament delivery mechanism to convert linear motion of the medicament delivery mechanism into torque so as to rotate a rotation member.

These and other aspects of the invention will be apparent from and elucidated with reference to the embodiments described hereinafter.

BRIEF DESCRIPTION OF THE FIGURES

Reference will now be made in detail to the embodiments, examples of which are illustrated in the accompanying drawings, wherein like reference numerals refer to like elements throughout.

DETAILED DESCRIPTION

Figure 1:
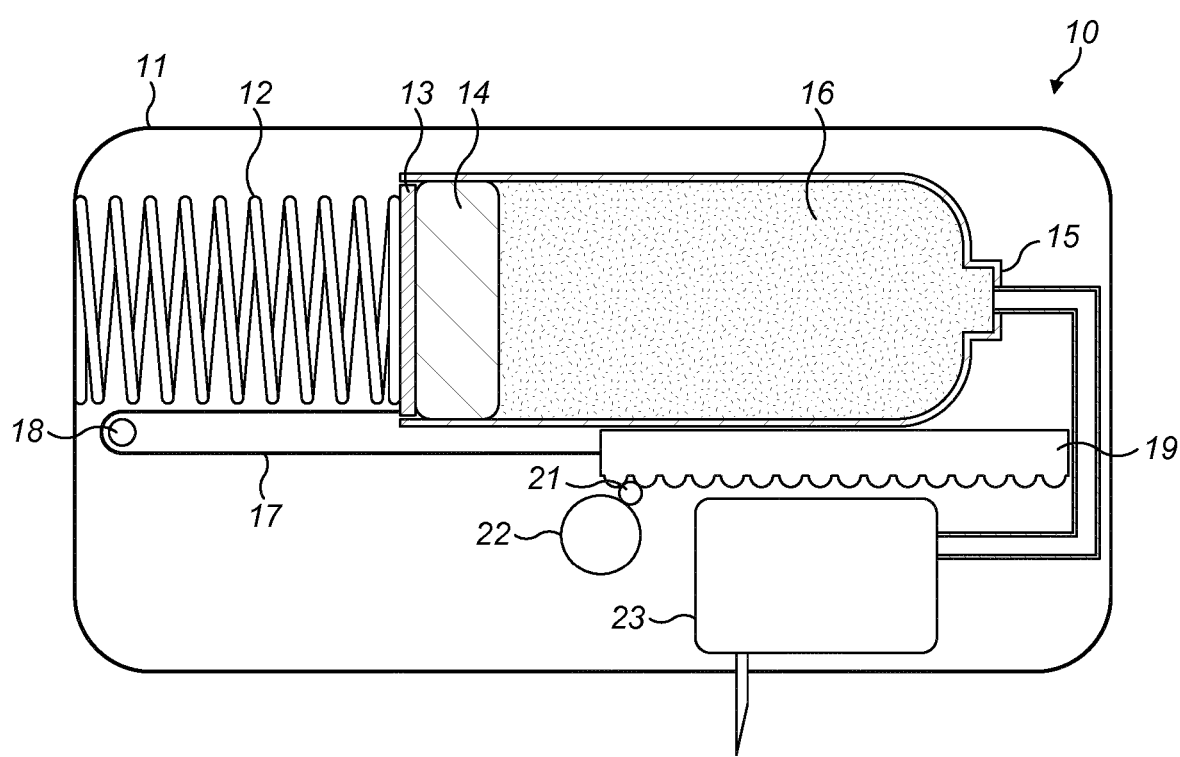
FIG. 1 is a schematic view of a medicament delivery device according to a first embodiment.

A medicament delivery device with a driving mechanism for rotating a rotation member is provided. The medicament delivery device comprises a housing arranged to contain a medicament container with a piston for sealing the medicament container and displacing the medicament; a medicament delivery mechanism arranged to push the piston to displace the medicament when activated; and a driving mechanism connected to the medicament delivery mechanism such that when the medicament delivery mechanism is activated, the driving mechanism converts linear motion of the medicament delivery mechanism into torque so as to rotate a rotation member.

By providing this torque to rotate the rotation member, an internal system can be driven. According to some embodiments, the internal mechanism may be an indicator system or an energy generating apparatus. Thus, the energy used for delivering medicament to a patient may be harvested for other purposes such as indicating to the patient an amount of medicament in the device or powering periphery systems in the medicament delivery device.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

FIG. 1 is a schematic view of a medicament delivery device according to a first embodiment. The device is described below in the context of a Large Volume Device (LVD), but it will be appreciated that it could alternatively be another type of bolus injector.

A medicament delivery device 10 according to a first embodiment of the invention is shown in FIG. 1. The medicament delivery device 10 comprises a housing 11 containing a medicament container 15 with an outlet. The medicament container 15 contains liquid medicament 16 which is sealed by a piston, stopper, or bung 14 located within the medicament container 15. In an initial state, the piston 14 is located at a position furthest away from the outlet of the medicament container 15.

A medicament delivery mechanism 12 is also located within the housing 11, the medicament delivery mechanism 12 being arranged to push the piston 14 towards the outlet of the medicament container 15 when it is activated. The outlet of the medicament container 15 is connected to a fluid path. One end of the fluid path is connected to the outlet of the medicament container 15 while another end of the fluid path is connected to a needle injection system 23. The needle injection system 23 includes a hollow injection needle through which medicament can be displaced when the piston 14 is pushed towards the outlet of the medicament container 15 and through the fluid path.

In the present embodiment, the medicament delivery mechanism 12 comprises a drive spring that is initially in a compressed state, storing spring energy that is to be released when the medicament delivery mechanism 12 is activated. A plate member 13 is arranged between the medicament delivery mechanism 12 and the piston 14. The plate member 13 is movable along with the piston 14, such that when the medicament delivery mechanism 12 is activated it exerts a pushing force on the plate member 13 and the piston 14. The plate member 13 in the present embodiment is fixedly attached to a cable 17, which is part of a driving mechanism.

The driving mechanism in the present embodiment further comprises a first pulley 18, a rack gear 19, a first pinion gear 21, and a rotation member 22. The cable 17 is passed over a periphery of the first pulley 18 such that direction of the force on the cable 17 is reversed at the first pulley 18. The first pinion gear 21 is rotatably engaged with the rack gear 19 and the rotation member 22 is rotatably engaged with the first pinion gear 21.

In this embodiment, as the plate member 13 is fixedly attached to the cable 17, when the plate member 13 moves linearly towards the outlet of the medicament container 15 under the pushing force exerted by the medicament delivery mechanism 12 in a first direction (i.e. towards the right in FIG. 1), a linear force is also exerted on the cable 17 in the first direction. The direction of this linear force is reversed at the first pulley 18 such that a force acts on a rack gear 19 in a second direction, the second direction being opposite from the first direction.

The rack gear 19 as shown in FIG. 1 compares a plurality of teeth arranged on its surface. The linear force exerted on the rack gear 19 in the second direction causes it to move linearly within a predetermined space. In the present embodiment, the rack gear 19 is pulled by the cable 17 towards the second direction and thus the plurality of teeth of the rack gear 19 mesh with the first pinion gear 21. The meshing action between the plurality of teeth of the rack gear 19 and the first pinion gear 21 causes a rotation of the first pinion gear 21. The rotation of the first pinion gear 21 in turn meshes with the rotation member 22 to cause rotation of the rotation member 22. In other words, the configuration of the driving mechanism in this embodiment converts linear motion of the medicament delivery mechanism into torque so as to rotate a rotation member 22. In this embodiment, the rotation member 22 is a gear wheel comprising a plurality of teeth on its periphery so as to facilitate meshing between the first pinion gear 21 and the rotation member 22.

As will be explained in further detail with respect to subsequent drawings, the rotation of the rotation member 22 is utilised for driving an internal apparatus or system, such as an energy generating apparatus and/or an indicator system.

Figure 2:
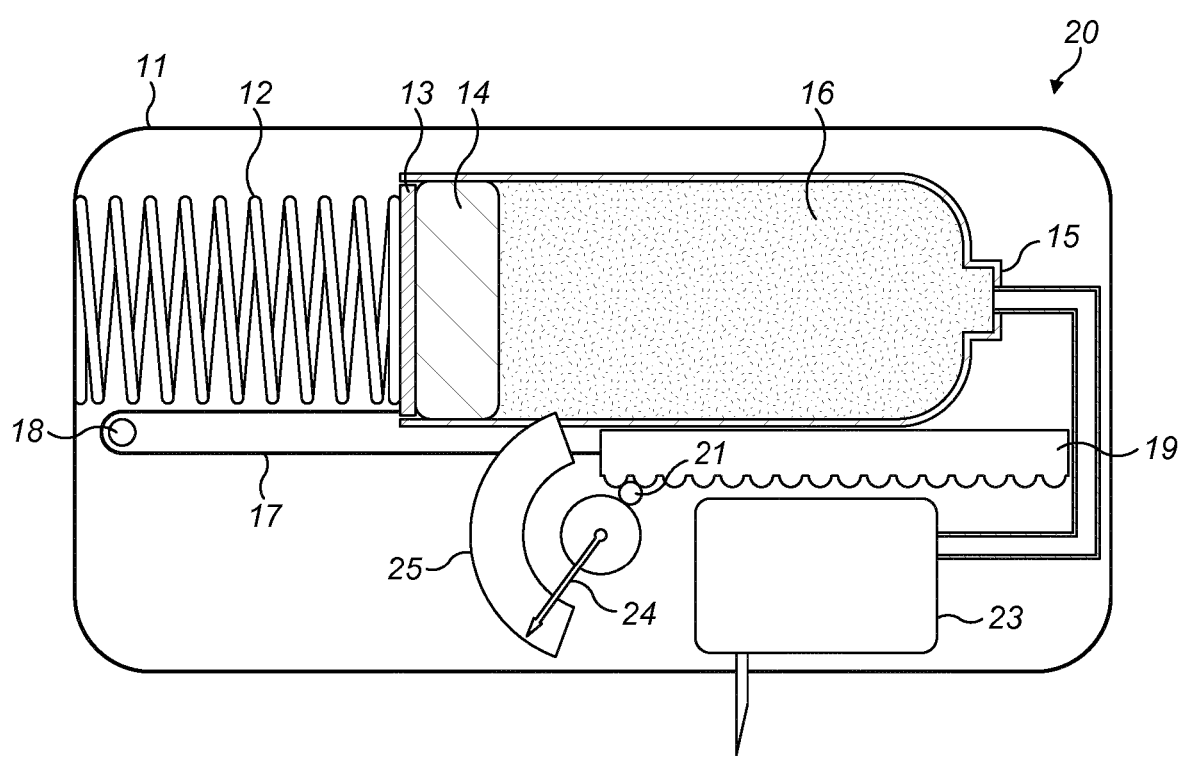
FIG. 2 is a schematic view of a medicament delivery device according to a second embodiment.

FIG. 2 is a schematic view of a medicament delivery device according to a second embodiment.

The medicament delivery device 20 of the second embodiment is similar to the medicament delivery device 10 of the first embodiment, with the addition of an indicator system comprising an indicator member 24 and a scale 25. In this embodiment the indicator member 24 is arranged on top of the scale 25 in this perspective view.

In this embodiment, the indicator member 24 of the indicator system is a narrow elongate member arranged at a surface of the rotation member 22 such that it extends from a centre of the rotation member 22 outwards. The indicator member 24 is fixedly attached to the rotation member 22 such that as the rotation member 22 rotates, an outer end of the indicator member 24 moves along the scale 25.

The scale 25 in this embodiment is a rotational scale having a curved shape so as to adapt to the sweeping motion of the outer end of the indicator member 24. A first end of the scale 25 represents when the medicament container 15 is full, and a second end of the scale 25 represents when the medicament container 15 is empty. Therefore, as the outer end of the indicator member 24 points along the scale 25, a user is able to determine an amount of medicament currently contained in this medicament container 15.

When the medicament delivery mechanism 12 is activated, the drive spring of the medicament delivery mechanism 12 releases to exert a pushing force on the plate member 13 and the piston 14. As the plate member 13 is fixedly attached to the cable 17, when the plate member 13 moves linearly towards the outlet of the medicament container 15 under the pushing force exerted by the medicament delivery mechanism 12 in a first direction (i.e. towards the right in FIG. 2), a linear force is also exerted on the cable 17 in the first direction. The direction of this linear force is reversed at the first pulley 18 such that a force acts on a rack gear 19 in a second direction, the second direction being opposite from the first direction.

The linear force exerted on the rack gear 19 in the second direction causes it to move linearly within the predetermined space. In the present embodiment, the rack gear 19 is pulled by the cable 17 towards the second direction and thus the plurality of teeth of the rack gear 19 mesh with the first pinion gear 21. The meshing action between the plurality of teeth of the rack gear 19 and the first pinion gear 21 causes a rotation of the first pinion gear 21. The rotation of the first pinion gear 21 in turn meshes with the rotation member 22 to cause rotation of the rotation member 22. In other words, the configuration of the driving mechanism in this embodiment results in the provision of torque to the rotation member 22.

Hence, as the medicament 16 contained in the medicament container 15 is being displaced through the outlet of the medicament container 15, the outer end of the indicator member 24 sweeps along the scale 25 from one end to another in order to allow the user to determine the amount of medicament currently contained in the medicament container 15.

A transparent window (not shown in FIG. 2) is provided at the housing 11 of the medicament delivery device 20 so as to allow a user to view through into an interior of the device 20, at the indicator system, so as to determine a position of the outer end of the indicator member 24 along the scale 25.

Figure 3A:
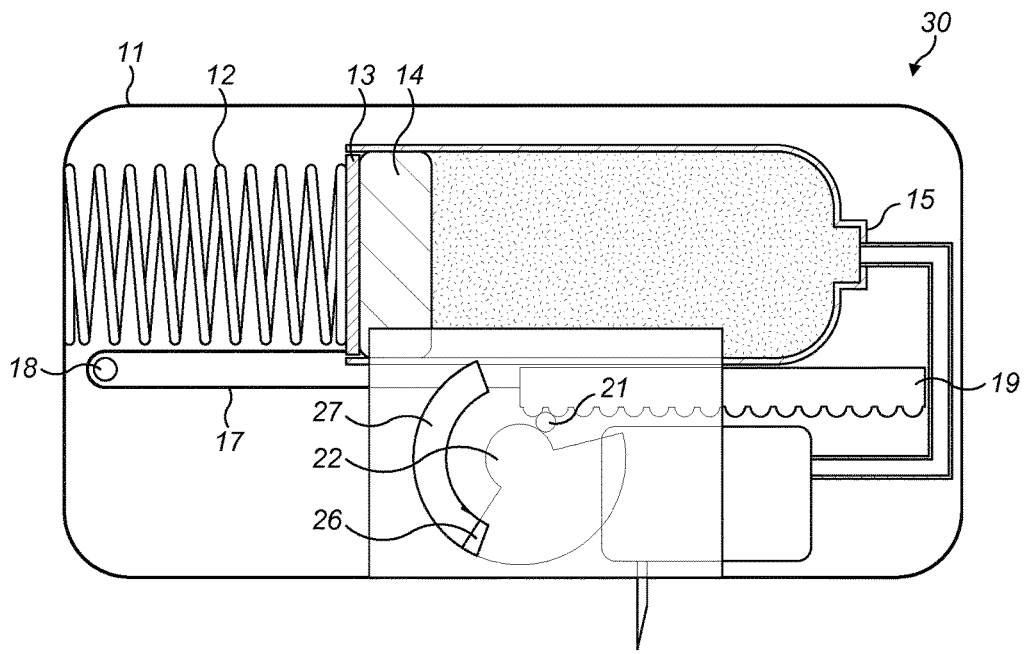
FIG. 3A is a schematic view of a medicament delivery device in an initial state, according to a third embodiment.
Figure 3B:
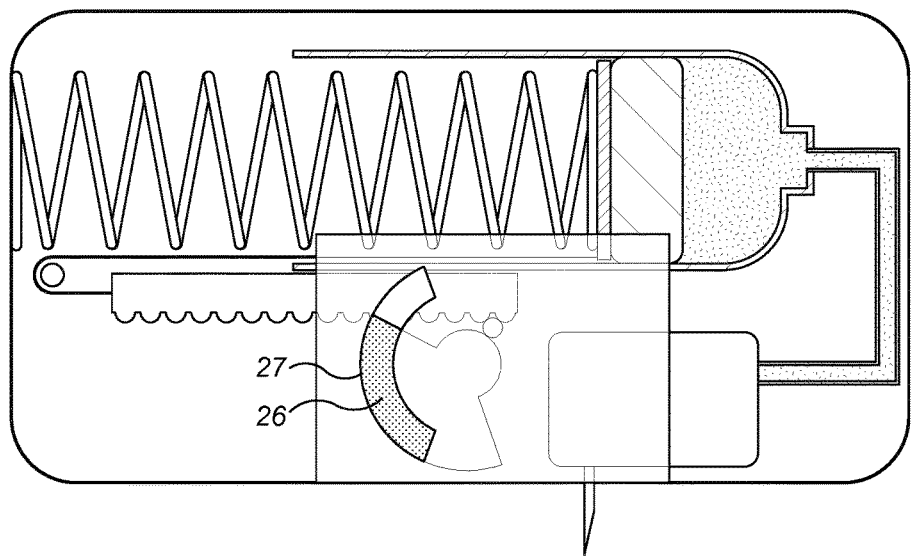
FIG. 3B is a schematic view of the medicament delivery device in a final state, according to the third embodiment.

FIGS. 3A and 3B are schematic views of a medicament delivery device in an initial state and a final state respectively, according to a third embodiment.

The medicament delivery device 30 of the third embodiment as shown in FIGS. 3A and 3B is similar to the medicament delivery device 10 of the first embodiment, with the addition of an indicator system comprising an indicator member 26 and a scale 27.

In this embodiment, the indicator member 26 of the indicator system is a fan-shaped member arranged at a surface of the rotation member 22 such that it extends from a center of the rotation member 22 outwards. The scale 27 is an arc-shaped aperture of a flat covering member arranged on top of the indicator member 26. The indicator member 26 is fixedly attached to the rotation member 22 such that as the rotation member 22 rotates, the indicator member 26 rotates so as to cover the arc-shaped aperture (scale 27).

The arc-shaped scale 27 in this embodiment is a rotational scale adapted to the sweeping motion of the indicator member 26 as it rotates. As shown in FIG. 3A, in an initial state, i.e. before injection, the indicator member 26 is in a position such that the arc-shaped scale 27 is substantially uncovered which represents when the medicament container 15 is full. As shown in FIG. 3B, in a final state, i.e. after injection, the indicator member 26 is in a position such that the arc-shaped scale 27 is fully covered which represents when the medicament container is empty. Therefore, as the indicator member 26 rotates due to the rotation of the rotation member 22, a user is able to determine an amount of medicament currently contained in this medicament container 15.

When the medicament delivery mechanism 12 is activated, the drive spring of the medicament delivery mechanism 12 releases to exert a pushing force on the plate member 13 and the piston 14. As the plate member 13 is fixedly attached to the cable 17, when the plate member 13 moves linearly towards the outlet of the medicament container 15 under the pushing force exerted by the medicament delivery mechanism 12 in a first direction (i.e. towards the right in FIGS. 3A and 3B), a linear force is also exerted on the cable 17 in the first direction. The direction of this linear force is reversed at the first pulley 18 such that a force acts on a rack gear 19 in a second direction, the second direction being opposite from the first direction.

The linear force exerted on the rack gear 19 in the second direction causes it to move linearly within the predetermined space. In the present embodiment, the rack gear 19 is pulled by the cable 17 towards the second direction and thus the plurality of teeth of the rack gear 19 mesh with the first pinion gear 21. The meshing action between the plurality of teeth of the rack gear 19 and the first pinion gear 21 causes a rotation of the first pinion gear 21. The rotation of the first pinion gear 21 in turn meshes with the rotation member 22 to cause rotation of the rotation member 22. In other words, the configuration of the driving mechanism in this embodiment results in the provision of torque to the rotation member 22.

Hence, as the medicament contained in the medicament container 15 is being displaced through the outlet of the medicament container 15, the indicator member 26 sweeps along the scale 27 to cover the arc-shaped aperture so as to allow the user to determine the amount of medicament currently contained in the medicament container 15.

Similar to the second embodiment, a transparent window (not shown in FIGS. 3A and 3B) is provided at the housing 11 of the medicament delivery device 30 so as to allow a user to view through into an interior of the device 30, at the indicator system, so as to determine a position of the indicator member 26 with respect to the scale 27.

Figure 4:
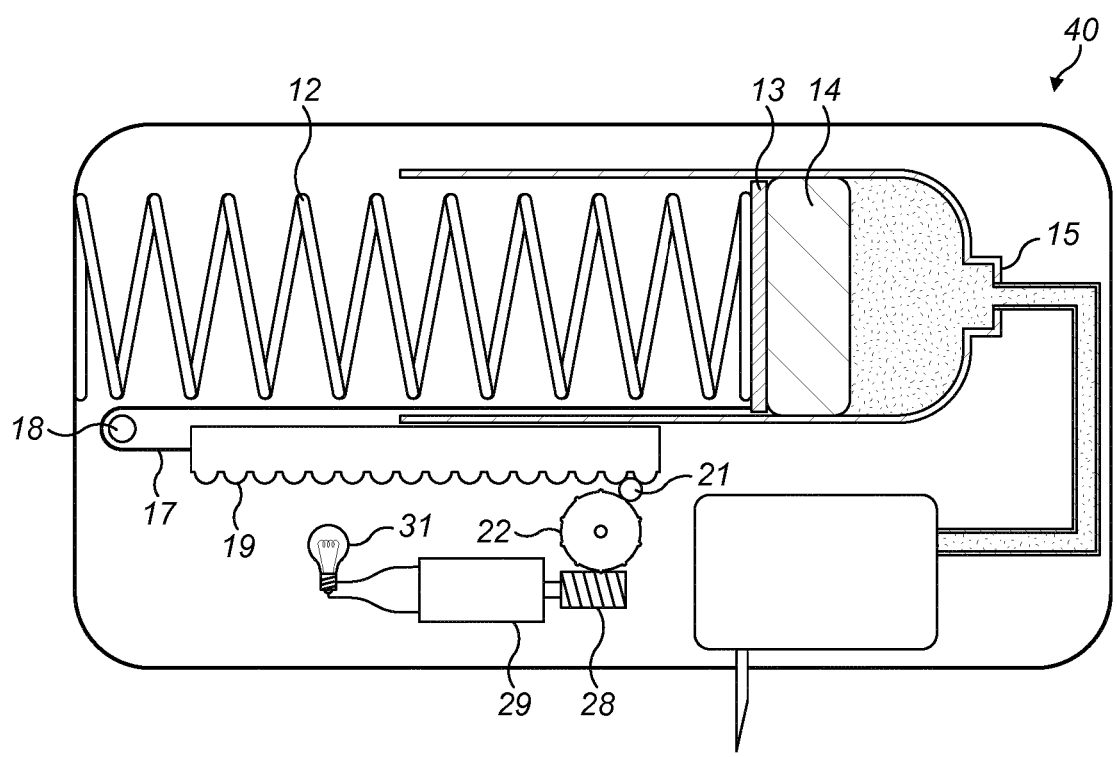
FIG. 4 is a schematic view of a medicament delivery device according to a fourth embodiment.

FIG. 4 is a schematic view of a medicament delivery device according to a fourth embodiment.

The medicament delivery device 40 of the fourth embodiment is similar to the medicament delivery device 10 of the first embodiment, with the addition of a worm screw 28, an energy generating apparatus 29, and a light source 31.

As shown in FIG. 4, in this embodiment the rotation member 22 is a worm wheel which forms a worm drive arrangement with a worm screw 28. The worm wheel 22 in this embodiment comprises a plurality of teeth which mesh with a threaded arrangement on an outer surface of the worm screw 28. In this worm drive arrangement, rotary motion is transmitted through a 90° angle. Specifically, the rotary motion of the worm wheel 22 in a first axis causes a rotary motion of the worm screw 28 in a second axis, the first axis being perpendicular to the second axis.

The worm screw 28 is mechanically connected to the energy generating apparatus 29. In this embodiment, the energy generating apparatus 29 comprises a dynamo which is configured to convert mechanical rotation into a direct electric current.

The energy generating apparatus 29 is electrically connected to a light source 31, which in this embodiment is a light-emitting diode (LED). Therefore, as energy generating apparatus 29 converts mechanical rotation of the worm screw 28, the light source 31 is powered.

When the medicament delivery mechanism 12 is activated, the drive spring of the medicament delivery mechanism 12 releases to exert a pushing force on the plate member 13 and the piston 14. As the plate member 13 is fixedly attached to the cable 17, when the plate member 13 moves linearly towards the outlet of the medicament container 15 under the pushing force exerted by the medicament delivery mechanism 12 in a first direction (i.e. towards the right in FIG. 4), a linear force is also exerted on the cable 17 in the first direction. The direction of this linear force is reversed at the first pulley 18 such that a force acts on a rack gear 19 in a second direction, the second direction being opposite from the first direction.

The linear force exerted on the rack gear 19 in the second direction causes it to move linearly within the predetermined space. In the present embodiment, the rack gear 19 is pulled by the cable 17 towards the second direction and thus the plurality of teeth of the rack gear 19 mesh with the first pinion gear 21. The meshing action between the plurality of teeth of the rack gear 19 and the first pinion gear 21 causes a rotation of the first pinion gear 21. The rotation of the first pinion gear 21 in turn meshes with the rotation member 22 to cause rotation of the rotation member 22. In other words, the configuration of the driving mechanism in this embodiment results in the provision of torque to the rotation member 22.

Hence, as the medicament contained in the medicament container 15 is being displaced through the outlet of the medicament container 15, the rotation member 22, which is a worm wheel in this embodiment, meshes with the worm screw 28 so as to transmit rotary motion through a 90° angle. As the worm screw 28 rotates, a current is generated by the energy generating apparatus to which the worm screw 28 is connected to. In the present embodiment, this generated energy is used to power the light source 31.

In alternative embodiments, the energy generating apparatus of the fourth embodiment may be electrically connected to an energy storing apparatus, such as a capacitor, instead of being connected directly to a light source. In these alternative embodiments, the energy (direct electric current) generated at the energy generating apparatus may be stored at the energy storing apparatus and may be used subsequently for powering on-board equipment at the device.

Figure 5A:
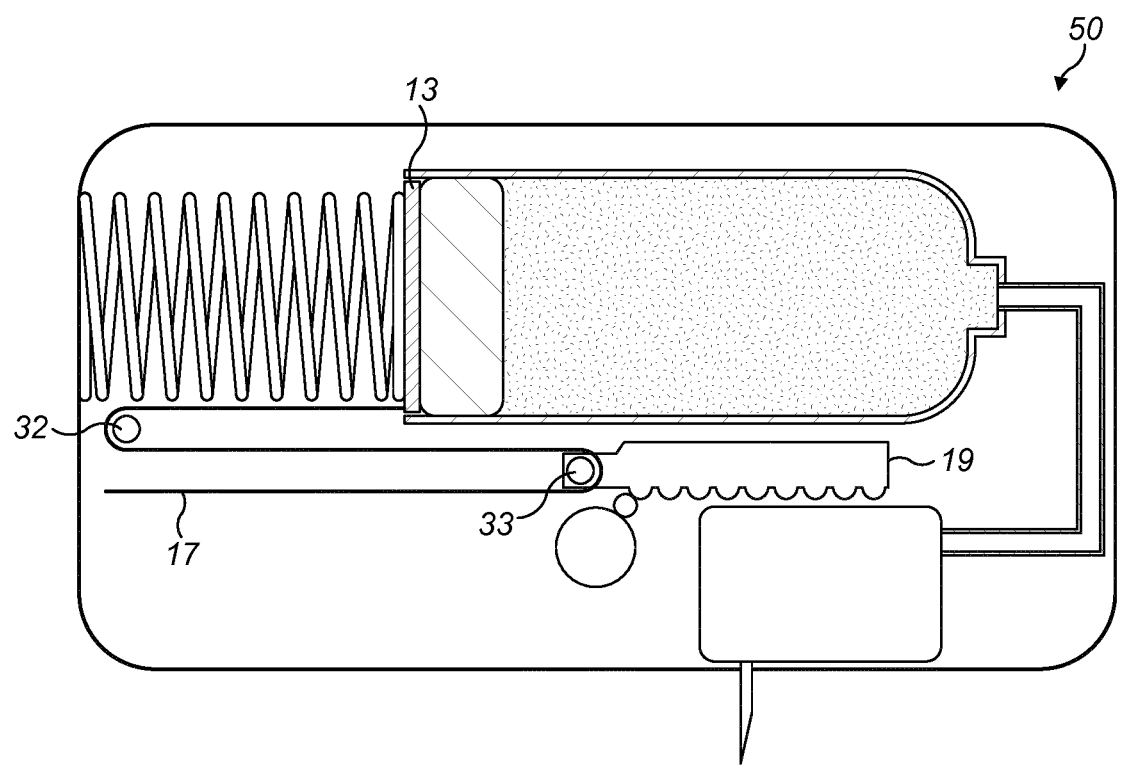
FIG. 5A is a schematic view of a medicament delivery device in an initial state according to a fifth embodiment.
Figure 5B:
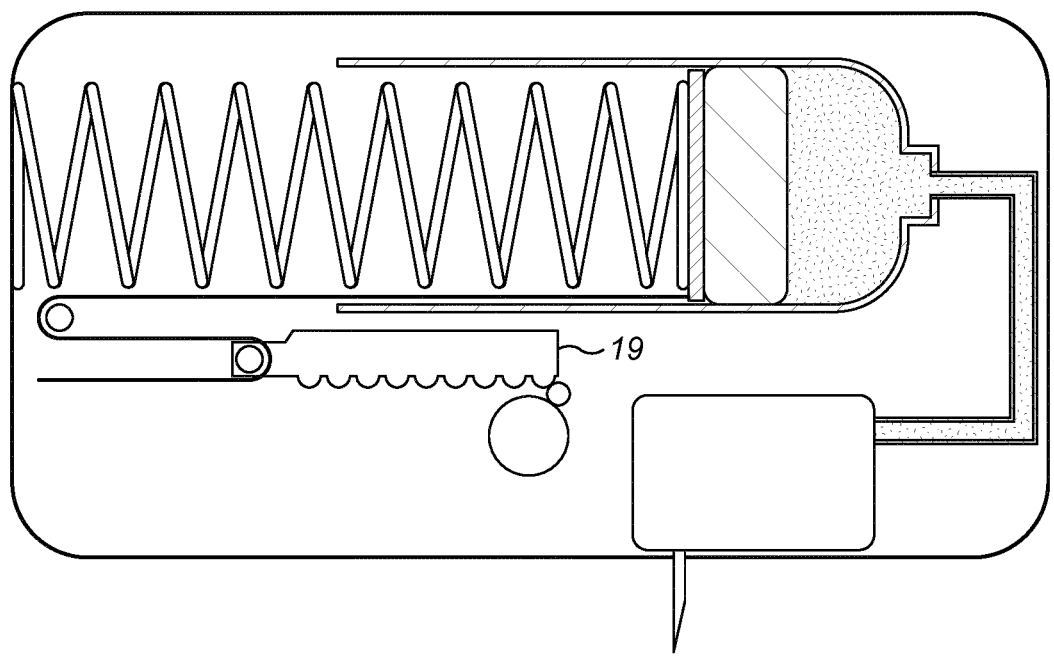
FIG. 5B is a schematic view of a medicament delivery device in a final state according to the fifth embodiment.

FIGS. 5A and 5B are schematic views of a medicament delivery device in an initial state and a final state respectively, according to a fifth embodiment.

The medicament delivery device 50 of the fifth embodiment as shown in FIGS. 5A and 5B is similar to the medicament delivery device 10 of the first embodiment. However, instead of using a singular pulley in the driving mechanism, in this embodiment the driving mechanism comprises a first pulley 32 and a second pulley 33 The cable 17 in this embodiment first passes over a periphery of the first pulley and then passes over a periphery of the second pulley 33 such that a linear force acting on the cable 17 at the connection between the cable 17 and the plate member 13 in the first direction (i.e. towards the right in FIG. 5A) is reversed at the first pulley 32, and then reversed again at the second pulley 32.

The second pulley 33 is rotatably mounted at the gear rack 19, and is at the same time movably mounted at the device 50 along with the gear rack 19 such that it can be moved linearly within a predetermined space in the device 50 with the gear rack 19. Therefore, when a pulling force is exerted on the second pulley 33, the second pulley 33 and the gear rack 19 are moved linearly towards the first pulley 32 (i.e. to the left in FIGS. 5A and 5B).

In this embodiment, a first end of the cable 17 is attached to the plate member 13, the plate member 13 being arranged between the medicament delivery mechanism 12 and the piston 14. A second end of the cable 17 is fixedly attached within the housing 11 of the device 50. Thus, when the medicament delivery mechanism 12 is activated to push the plate member 13 and the piston 14 towards the outlet of the medicament container 15, a pushing force also acts on the first end of the cable 17 such that it moves linearly with the plate member 13.

The direction of this linear force is reversed at the first pulley 32 such that a force acts on the second pulley 33 in a second direction, the second direction being opposite from the first direction. This force acts to pull the second pulley 33 and the gear rack 19 towards the second direction, such that the plurality of teeth of the rack gear 19 mesh with the first pinion gear 21. The rotation of the first pinion gear 21 in turn meshes with the rotation member 22 to cause rotation of the rotation member 22. In other words, the configuration of the driving mechanism in this embodiment results in the provision of torque to the rotation member 22. As illustrated in FIGS. 5A and 5B, the gear rack 19 moves from an initial position (in FIG. 5A) to a final position (in FIG. 5B) due to the pulling force towards the second direction as the medicament delivery mechanism 12 pushes the plate member 13 and the piston 13 towards the outlet of the medicament container 15.

The use of two pulleys in the driving mechanism in the present embodiment, compared to the first embodiment, would allow the use of a shorter gear rack. This is beneficial for devices which have certain dimensional constraints due to the sizes of other components in the device or manufacture requirements.

Figure 6A:
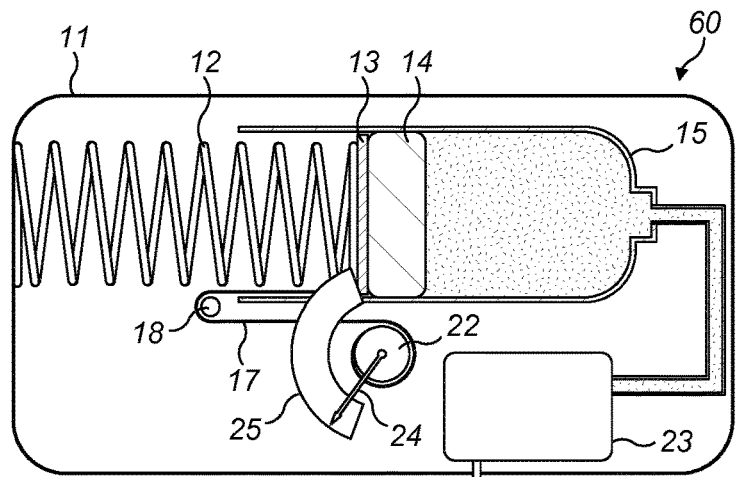
FIG. 6A is a schematic view of a medicament delivery device according to a sixth embodiment.
Figure 6B:
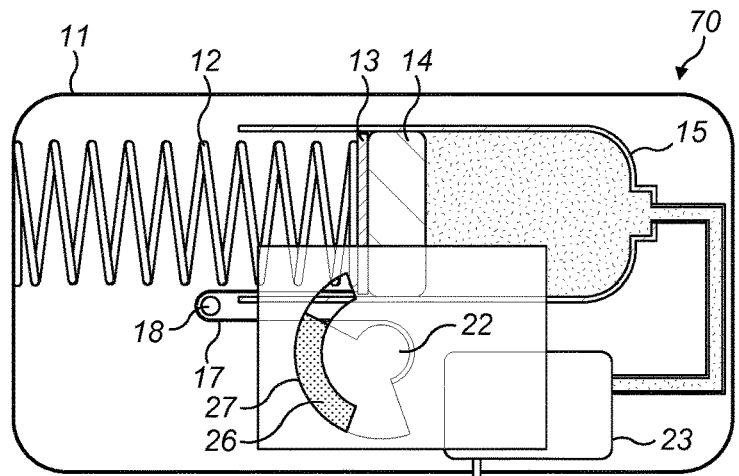
FIG. 6B is a schematic view of a medicament delivery device according to a seventh embodiment.
Figure 6C:
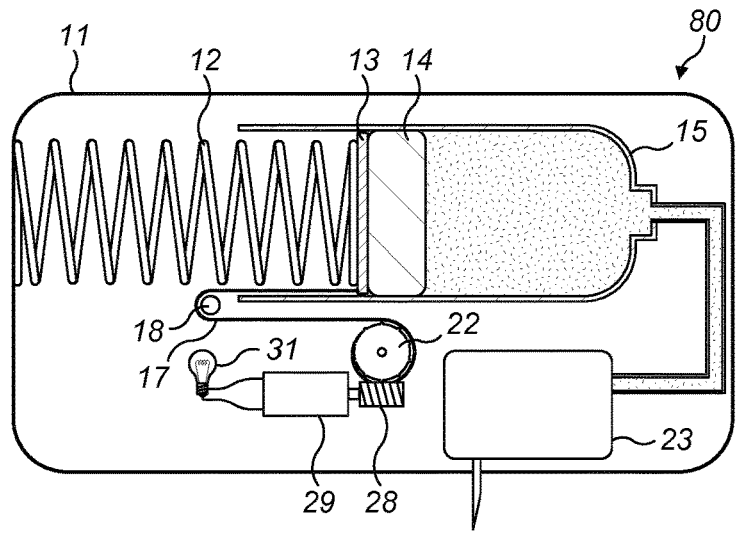
FIG. 6C is a schematic view of a medicament delivery device according to an eighth embodiment.

FIG. 6A is a schematic view of a medicament delivery device according to a sixth embodiment. FIG. 6B is a schematic view of a medicament delivery device according to a seventh embodiment. FIG. 6C is a schematic view of a medicament delivery device according to an eighth embodiment.

The sixth, seventh, and eighth embodiments as respectively shown in FIGS. 6A to 6C adopt a similar configuration. In these embodiments, the medicament delivery device 60, 70, 80 each comprises a housing 11 containing a medicament container 15 with an outlet. The medicament container 15 contains liquid medicament 16 which is sealed by a piston, stopper, or bung 14 located within the medicament container 15. In an initial state, the piston 14 is positioned at a position furthest away from the outlet of the medicament container 15.

A medicament delivery mechanism 12 is also located within the housing 11, the medicament delivery 12 being arranged to push the piston 14 towards the outlet of the medicament container 15 once it is activated. The outlet of the medicament container 15 is connected to a fluid path. One end of the fluid path is connected to the outlet of the medicament container 15 while another end of the fluid path is connected to a needle injection system 23. The needle injection system 23 includes a hollow injection needle through which medicament can be displaced when the piston 14 is pushed towards the outlet of the medicament container 15 and through the fluid path.

In the sixth, seventh, and eighth embodiments, the medicament delivery mechanism 12 comprises a drive spring that is initially in a compressed state, storing spring energy that is to be released when the medicament delivery mechanism 12 is activated. A plate member 13 is arranged between the medicament delivery mechanism 12 and the piston 14, such that when the medicament delivery mechanism 12 is activated it exerts a pushing force on the plate member 13 and the piston 14. The plate member 13 in the present embodiments is fixedly attached to a cable 17, which is part of a driving mechanism.

The driving mechanism in the present embodiments further comprises a first pulley 18 and a rotation member 22. The cable 17 is passed over a periphery of the first pulley 18 such that direction of the force on the cable 17 is reversed at the first pulley 18. The cable is then passed over a periphery of the rotation member 22. The first end of the cable 17 is fixedly attached to the plate member 13 while the second end of the cable 17 is fixedly attached to the rotation member 22. Hence, as the plate member 13 moves linearly towards the outlet of the medicament container 15 under the pushing force exerted by the medicament delivery mechanism 12 in a first direction (i.e. towards the right in FIGS. 6A, 6B, and 6C), a linear force is also exerted on the cable 17 in the first direction. The direction of this linear force is reversed at the first pulley 18 such that a force acts on the rotation member 22 in a second direction, the second direction being opposite from the first direction.

In other words, the configuration of the driving mechanism in these embodiments converts linear motion of the medicament delivery mechanism into torque so as to rotate a rotation member 22. In the sixth and seventh embodiments, the rotation member 22 is a wheel comprising a roughened outer surface so as to maximize friction between a periphery of the rotation member 22 and the cable 17. In the eighth embodiment, the rotation member 22 is a worm wheel arranged to mesh with a worm screw. This will be explained in further detail with respect to FIG. 6C.

The difference between the sixth, seventh, and eighth embodiments is that the rotation member 22 in each of these embodiments is connected to a different internal system.

As shown in FIG. 6A, in the sixth embodiment, the rotation member 22 is connected to an indicator system comprising an indicator member 24 and a scale 25. In this embodiment, the indicator member 24 of the indicator system is a narrow elongate member arranged at a surface of the rotation member such that it extends from a centre of the rotation member 22 outwards. Also, the indicator member 24 is arranged on top of the scale. The indicator member 24 is fixedly attached to the rotation member 22 such that as the rotation member 22 rotates, an outer end of the indicator member 24 moves along the scale 25.

The scale 25 in this embodiment has a curved shape so as to adapt to the sweeping motion of the outer end of the indicator member 24. A first end of the scale 25 represents when the medicament container 15 is full, and a second end of the scale 25 represents when the medicament container 15 is empty. Therefore, as the outer end of the indicator member 24 points along the scale 25 as the medicament delivery mechanism 12 pushes the plate member 13 towards the outlet of the medicament container 15, a user is able to determine an amount of medicament currently contained in this medicament container 15.

A transparent window (not shown in FIG. 6A) is provided at the housing 11 of the medicament delivery device 60 so as to allow a user to view through into an interior of the device 60, at the indicator system, so as to determine a position of the outer end of the indicator member 24 along the scale 25.

As shown in FIG. 6B, in the seventh embodiment, the rotation member 22 is connected to an indicator system comprising an indicator member 26 and a scale 27.

In this embodiment, the indicator member 26 of the indicator system is a fan-shaped member arranged at a surface of the rotation member 22 such that it extends from a centre of the rotation member 22 outwards. The scale 27 is an arc-shaped aperture of a flat covering member arranged on top of the indicator member 26. The indicator member 26 is fixedly attached to the rotation member 22 such that as the rotation member 22 rotates, the indicator member 26 rotates so as to cover the arc-shaped aperture (scale 27).

The arc-shaped scale 27 in this embodiment is adapted to the sweeping motion of the indicator member 26 as it rotates. Therefore, as the indicator member 26 rotates due to the rotation of the rotation member 22, a user is able to determine an amount of medicament currently contained in this medicament container 15.

As shown in FIG. 6C, in the eighth embodiment, the rotation member 22 is a worm wheel which forms a worm drive arrangement with a worm screw 28. The worm wheel 22 in this embodiment comprises a plurality of teeth which mesh with a threaded arrangement on an outer surface of the worm screw 28. In this worm drive arrangement, rotary motion is transmitted through a 90° angle. Specifically, the rotary motion of the worm wheel 22 in a first axis causes a rotary motion of the worm screw 28 in a second axis, the first axis being perpendicular to the second axis.

The worm screw 28 is mechanically connected to the energy generating apparatus 29. In this embodiment, the energy generating apparatus 29 comprises a dynamo which is configured to convert mechanical rotation into a direct electric current.

The energy generating apparatus 29 is electrically connected to a light source 31, which in this embodiment is a light-emitting diode (LED). Therefore, as energy generating apparatus 29 converts mechanical rotation of the worm screw 28, the light source 31 is powered.

As described above, as the medicament contained in the medicament container 15 is being displaced through the outlet of the medicament container 15, the rotation member 22, which is a worm wheel in this embodiment, meshes with the worm screw 28 so as to transmit rotary motion through a 90° angle. As the worm screw 28 rotates, a current is generated by the energy generating apparatus to which the worm screw 28 is connected to. In the present embodiment, this generated energy is used to power the light source 31.

In alternative embodiments, the medicament delivery device may be a pen injector instead of a bolus injector.

In alternative embodiments, a linear scale may be used instead of a rotational and/or curved scale in the indicator system.

In alternative embodiments, the driving mechanism may comprise additional gear elements.

In alternative embodiments, the energy generating apparatus of the eighth embodiment may be electrically connected to an energy storing apparatus, such as a capacitor, instead of being connected directly to a light source. In these alternative embodiments, the energy (direct electric current) generated at the energy generating apparatus may be stored at the energy storing apparatus and may be used subsequently for powering on-board equipment at the device.

In alternative embodiments, the medicament delivery device may not comprise a plate member between the piston and the medicament delivery mechanism. In these alternative embodiments, an alternative mechanical member may be used for connecting the medicament delivery mechanism and the driving mechanism such that a linear motion of the medicament delivery mechanism can be converted into torque by the driving mechanism.

In alternative embodiments, the medicament delivery mechanism may not comprise a drive spring. In these alternative embodiments, other types of driving elements may be used to exert a pushing force on the piston in the medicament container. For example, a hydraulic mechanism may be employed for exerting a pushing force on the piston. As another example, a resilient deformable material may be used in place of the drive spring to provide a driving force. In some of these alternative embodiments, the medicament delivery mechanism may comprise a plunger element.

In alternative embodiments, the medicament delivery device may not be provided with a transparent window at the housing. In these alternative embodiments, the housing of the medicament delivery device may be made of transparent material so as to allow a user to view a status of the indicator system.

Although claims have been formulated in this application to particular combinations of features, it should be understood that the scope of the disclosure also includes any novel features or any novel combinations of features disclosed herein either explicitly or implicitly or any generalisation thereof, whether or not it relates to the same invention as presently claimed in any claim and whether or not it mitigates any or all of the same technical problems as does the present invention. The applicant hereby gives notice that new claims may be formulated to such features and/or combinations of features during the prosecution of the present application or of any further application derived therefrom.

Those skilled in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Examples of GLP-1, GLP-1 analogues and GLP-1 receptor agonists are, for example, Lixisenatide (Lyxumia®, Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The invention claimed is:

1. A medicament delivery device comprising:
   a housing arranged to contain a medicament container with a piston for sealing the medicament container and displacing a medicament in the medicament container;
   a medicament delivery mechanism arranged to push the piston to displace the medicament when activated; and
   a driving mechanism connected to the medicament delivery mechanism such that when the medicament delivery mechanism is activated, the driving mechanism converts linear motion of the medicament delivery mechanism into torque so as to rotate a rotation member;
   wherein the rotation member is connected to an indicator system comprising an indicator member and a scale;
   wherein the scale is fixed relative to the housing; and
   wherein the indicator member is arranged at the rotation member such that rotation of the rotation member causes the indicator member to move along the scale to indicate an amount of the medicament contained in the medicament container.

2. The medicament delivery device of claim 1, wherein a first end of the scale represents a full medicament container and a second end of the scale represents an empty medicament container.

3. The medicament delivery device of claim 1, wherein the driving mechanism comprises a plate member arranged between the medicament delivery mechanism and the piston.

4. The medicament delivery device of claim 3, wherein the driving mechanism further comprises a first pulley, a cable passed over a periphery of the first pulley, and wherein the cable passes over the rotation member.

5. The medicament delivery device of claim 4, wherein the driving mechanism further comprises a second pulley, and wherein the cable is passed over a periphery of the second pulley and the second pulley is configured to move a rack gear.

6. The medicament delivery device of claim 3, wherein the driving mechanism further comprises a first pulley, a cable passed over a periphery of the first pulley, a gear rack connected to the cable, and a first pinion gear rotatably engaged with the gear rack, wherein the plate member is fixedly attached to the cable and the first pinion gear is rotatably engaged with the rotation member.

7. The medicament delivery device of claim 1, wherein the medicament delivery device is a bolus injector.

8. The medicament delivery device of claim 1, wherein the medicament is a liquid medicament.

* * * * *